(12) United States Patent
Zhang et al.

(10) Patent No.: US 9,476,887 B2
(45) Date of Patent: Oct. 25, 2016

(54) SCREENING OF PROTEIN CANDIDATES

(75) Inventors: Jianbing Zhang, Ottawa (CA); Tomoko Hirama, Tokyo (JP)

(73) Assignee: National Research Council of Canada, Ottawa, Ontario (CA)

( * ) Notice: Subject to any disclaimer, the term of this patent is extended or adjusted under 35 U.S.C. 154(b) by 1166 days.

(21) Appl. No.: 13/390,967

(22) PCT Filed: Aug. 18, 2010

(86) PCT No.: PCT/CA2010/001267
§ 371 (c)(1),
(2), (4) Date: Feb. 17, 2012

(87) PCT Pub. No.: WO2011/020183
PCT Pub. Date: Feb. 24, 2011

(65) Prior Publication Data
US 2012/0178110 A1    Jul. 12, 2012

Related U.S. Application Data

(63) Continuation of application No. PCT/CA2009/001501, filed on Oct. 14, 2009.

(60) Provisional application No. 61/272,119, filed on Aug. 18, 2009.

(51) Int. Cl.
G01N 33/557    (2006.01)
G01N 33/68     (2006.01)
C12N 15/62     (2006.01)

(52) U.S. Cl.
CPC ........... *G01N 33/6803* (2013.01); *C12N 15/62* (2013.01); *G01N 33/557* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 2004/0229915 A1* | 11/2004 | Quibell et al. | 514/326 |
| 2006/0211619 A1* | 9/2006 | Steward et al. | 514/12 |
| 2009/0005257 A1* | 1/2009 | Jespers et al. | 506/9 |

(Continued)

FOREIGN PATENT DOCUMENTS

| | | |
|---|---|---|
| WO | 2010043057 | 4/2010 |
| WO | 2010045225 | 4/2010 |

(Continued)

OTHER PUBLICATIONS

Arbabi-Ghahroudi, M.,Tanha, J. & MacKenzie, R. (2009b). Isolation of monoclonal antibody fragments from phage display libraries. Methods Mol Biol 502, 341-64.

(Continued)

*Primary Examiner* — Mark Shibuya
*Assistant Examiner* — Richard Moerschell
(74) *Attorney, Agent, or Firm* — Roula Thomas

(57) ABSTRACT

Successful application of an engineered protein as therapeutics or in other industries would require the protein to have good expression level, good biophysical properties and often desired affinity to its target. The present invention provides a method of screening large numbers of protein candidates (PCs) in all three aspects simultaneously. PCs are fused to a protein anchor, which is captured by the target/antigen. The captured PCs are evaluated for their expression levels, biophysical properties and affinities using conventional methods.

7 Claims, 5 Drawing Sheets ompA:  MKKTAIAIAVALAGFATVAQA
L:     GGGGSGGGGSGGGGS
H:     DLNHHHHHH

(56) References Cited

U.S. PATENT DOCUMENTS

2009/0285825 A1* 11/2009 Kini et al. .................. 424/141.1
2011/0318348 A1* 12/2011 Zhang et al. .............. 424/135.1

FOREIGN PATENT DOCUMENTS

| WO | WO2010/043057 | * | 4/2010 | ............ | C07K 16/18 |
|----|---------------|---|--------|--------------|------------|
| WO | 2011020183    |   | 2/2011 |              |            |

OTHER PUBLICATIONS

Arbabi-Ghahroudi, M., To, R., Gaudette, N., Hirama, T., Ding, W., MacKenzie, R. & Tanha, J. (2009a). Aggregation-resistant VHs selected by in vitro evolution tend to have disulfide-bonded loops and acidic isoelectric points. Protein Eng Des Sel 22, 59-66.

Binz, H. K., Amstutz, P., Kohl, A., Stumpp, M. T., Briand, C., Forrer, P., Grutter, M. G. & Pluckthun, A. (2004). High-affinity binders selected from designed ankyrin repeat protein libraries. Nat Biotechnol 22, 575-82.

Christ, D., Famm, K. & Winter, G. (2007). Repertoires of aggregation-resistant human antibody domains. Protein Eng Des Sel 20, 413-6.

Dumoulin, M., Conrath, K., Van Meirhaeghe, A., Meersman, F., Heremans, K., Frenken, L. G., Muyldermans, S., Wyns, L. & Matagne, A. (2002). Single-domain antibody fragments with high conformational stability. Protein Sci 11, 500-15.

European Patent Office Communication dated Mar. 20, 2012 for EP Application No. 10809397.2.

European Patent Office Communication dated Mar. 30, 2012 for EP Application No. 10809397.2.

Ewert, S., Honegger, A. & Pluckthun, A. (2003). Structure-based improvement of the biophysical properties of immunoglobulin VH domains with a generalizable approach. Biochemistry 42, 1517-28.

Famm, K., Hansen, L., Christ, D. & Winter, G. (2008). Thermodynamically stable aggregation-resistant antibody domains through directed evolution. J Mol Biol 376, 926-31.

Hamers-Casterman, C., Atarhouch, T., Muyldermans, S., Robinson, G., Hamers, C., Songa, E. B., Bendahman, N. & Hamers, R. (1993). Naturally occurring antibodies devoid of light chains. Nature 363, 446-8.

Honegger, A., Malebranche, A. D., Rothlisberger, D. & Pluckthun, A. (2009). The influence of the framework core residues on the biophysical properties of immunoglobulin heavy chain variable domains. Protein Eng Des Sel 22, 121-34.

International Preliminary Report on Patentability dated Feb. 21, 2012 for PCT/CA2010/001267.

International Search Report dated Nov. 16, 2010 for PCT/CA2010/001267.

Jespers, L., Schon, O., Famm, K. & Winter, G. (2004). Aggregation-resistant domain antibodies selected on phage by heat denaturation. Nat Biotechnol 22, 1161-5.

Jonsson, A., Dogan, J., Herne, N., Abrahmsen, L. & Nygren, P. A. (2008). Engineering of a femtomolar affinity binding protein to human serum albumin. Protein Eng Des Sel 21, 515-27.

Kery, V., Savage, J. R., Widjaja, K., Blake, B. K., Conklin, D. R., Ho, Y. S., Long, X., von Rechenberg, M., Zarembinski, T. I. & Boniface, J. J. (2003). Expression screen by enzyme-linked immunofiltration assay designed for high-throughput purification of affinity-tagged proteins. Anal Biochem 317, 255-8.

Kohl, A., Binz, H. K., Forrer, P., Stumpp, M. T., Pluckthun, A. & Grutter, M. G. (2003). Designed to be stable: Crystal structure of a consensus ankyrin repeat protein. Proc Natl Acad Sci U S A 100, 1700-5.

Lehmann, M., Kostrewa, D., Wyss, M., Brugger, R., D'Arcy, A., Pasamontes, L. & van Loon, A. P. (2000). From DNA sequence to improved functionality: Using protein sequence comparisons to rapidly design a thermostable consensus phytase. Protein Eng 13, 49-57.

Leonard, P., Safsten, P., Hearty, S., McDonnell, B., Finlay, W. & O'Kennedy, R. (2007). High throughput ranking of recombinant avian scFv antibody fragments from crude lysates using the Biacore A100. J Immunol Methods 323, 172-9.

Li, S., Zheng, W., Kuolee, R., Hirama, T., Henry, M., Makvandi-Nejad, S., Fjallman, T., Chen, W. & Zhang, J. (2009). Pentabody-mediated antigen delivery induces antigen-specific mucosal immune response. Mol Immunol 46, 1718-1726.

Niesen, F. H., Koch, A., Lenski, U., Harttig, U., Roske, Y., Heinemann, U. & Hofmann, K. P. (2008). An approach to quality management in structural biology: biophysical selection of proteins for successful crystallization. J Struct Biol 162, 451-9.

Saerens, D., Pellis, M., Loris, R., Pardon, E., Dumoulin, M., Matagne, A., Wyns, L., Muyldermans, S. & Conrath, K. (2005). Identification of a universal VHH framework to graft non-canonical antigen-binding loops of camel single-domain antibodies. J Mol Biol 352, 597-607.

Schmid, F. X. (1997). Optical Spetroscopy to Characterize Protein Conformation and Conformational Change. In Protein Structure, A Practical Approach (Creighton, T. E., ed.), pp. 266-297. Oxford University Press.

Tanha, J., Muruganandam, A. & Stanimirovic, D. (2003). Phage display technology for identifying specific antigens on brain endothelial cells. Methods Mol Med 89, 435-49.

To, R., Hirama, T., Arbabi-Ghahroudi, M., MacKenzie, R., Wang, P., Xu, P., Ni, F. & Tanha, J. (2005). Isolation of monomeric human V(H)s by a phage selection. J Biol Chem 280, 41395-403.

Ueda, H., Kristensen, P. & Winter, G. (2004). Stabilization of antibody V-H-domains by proteolytic selection. Journal of Molecular Catalysis B Enzymatic 28, 173-179.

Woestenenk, E. A., Hammarstrom, M., Hard, T. & Berglund, H. (2003). Screening methods to determine biophysical properties of proteins in structural genomics. Anal Biochem 318, 71-9.

Written Opinion dated Nov. 16, 2010 for PCT/CA2010/001267.

Zhang, J., Tanha, J., Hirama, T., Khieu, N. H., To, R., Tong-Sevinc, H., Stone, E., Brisson, J. R. & MacKenzie, C. R. (2004). Pentamerization of single-domain antibodies from phage libraries: A novel strategy for the rapid generation of high-avidity antibody reagents. J Mol Biol 335, 49-56.

European Office Action issued for corresponding European Patent Application No. 10809397.2 issued Apr. 24, 2015.

* cited by examiner ompA: MKKTAIAIAVALAGFATVAQA
L: GGGGSGGGGSGGGGS
H: DLNHHHHHH

SEQUENCE LISTING

<160> NUMBER OF SEQ ID NOS: 13

<210> SEQ ID NO 1
<211> LENGTH: 372
<212> TYPE: DNA
<213> ORGANISM: lama glama

<400> SEQUENCE: 1

```
caggtaaagc tggaggagtc tggggagga ctggtgcagg ttggggactc tctgagactc        60
tcctgtgcag cctccggacg caccttcagt aactatacca tggcctggtt ccgccagttt       120
ccagggaagg agcgtgagtt tgtagcagta gttagtcggg ggggtggcgc cacagactat       180
gcagactccg tgaagggccg attcaccatc tccagagaca acgccaagaa caccatgtat       240
ctgcaaatga acagcctgaa aactgaggac acggccgtct attactgtgc agcgggtaca       300
gacctaagtt actattacag cacaaaaaaa tgggcctact ggggccaggg gacccaggtc       360
accgtctcct ca                                                           372
```

<210> SEQ ID NO 2
<211> LENGTH: 124
<212> TYPE: PRT
<213> ORGANISM: lama glama

<400> SEQUENCE: 2

```
Gln Val Lys Leu Glu Glu Ser Gly Gly Gly Leu Val Gln Val Gly Asp
 1               5                  10                  15

Ser Leu Arg Leu Ser Cys Ala Ala Ser Gly Arg Thr Phe Ser Asn Tyr
```

```
              20                  25                  30
Thr Met Ala Trp Phe Arg Gln Phe Pro Gly Lys Glu Arg Glu Phe Val
         35                  40                  45

Ala Val Val Ser Arg Gly Gly Ala Thr Asp Tyr Ala Asp Ser Val
 50                  55                  60

Lys Gly Arg Phe Thr Ile Ser Arg Asp Asn Ala Lys Asn Thr Met Tyr
 65                  70                  75                  80

Leu Gln Met Asn Ser Leu Lys Thr Glu Asp Thr Ala Val Tyr Tyr Cys
             85                  90                  95

Ala Ala Gly Thr Asp Leu Ser Tyr Tyr Tyr Ser Thr Lys Lys Trp Ala
            100                 105                 110

Tyr Trp Gly Gln Gly Thr Gln Val Thr Val Ser Ser
            115                 120
```

<210> SEQ ID NO 3
<211> LENGTH: 843
<212> TYPE: DNA
<213> ORGANISM: Artificial
<220> FEATURE:
<223> OTHER INFORMATION: pBSA12 vector

<400> SEQUENCE: 3

```
tagagggtag aattcatgaa aaaaccgct atcgcgatcg cagttgcact ggctggtttc      60
gctaccgttg cgcaggccca gccggcccag gtgcacctgc agtctgcggc cgcgggccag    120
gccggccagg gatccggtgg aggcgggtcc ggtggaggcg gtccggtgg aggcgggtcc    180
caggtaaagc tggaggagtc tggggggagga ctggtgcagg ttggggactc tctgagactc    240
tcctgtgcag cctccggacg caccttcagt aactatacca tggcctggtt ccgccagttt    300
ccagggaagg agcgtgagtt tgtagcagta gttagtcggg gggtggcgc acagactat     360
gcagactccg tgaagggccg attcaccatc tccagagaca cgccaagaa caccatgtat    420
ctgcaaatga acagcctgaa aactgaggac acggccgtct attactgtgc agcgggtaca    480
gacctaagtt actattacag cacaaaaaaa tgggcctact ggggccaggg acccaggtc    540
accgtctcct cagatctgaa ccatcaccat caccatcact agtgaaagct ggcactggc    600
cgtcgtttta acgtcgtg actgggaaaa ccctggcgtt acccaactta atcgccttgc    660
agcacatccc cctttcgcca gctggcgtaa tagcgaagag gcccgcaccg atcgcccttc    720
caacagttgc gcagcctgaa tggcgaatgg cgcctgatgc ggtattttct ccttacgcat    780
ctgtgcggta tttcacaccg catatggtgc actctcagta caatctgctc tgatgccgca    840
tag                                                                  843
```

<210> SEQ ID NO 4
<211> LENGTH: 77
<212> TYPE: DNA
<213> ORGANISM: Artificial
<220> FEATURE:
<223> OTHER INFORMATION: Forward primer

<400> SEQUENCE: 4

```
cgggatccgg tggaggcggg tccggtggag gcgggtccgg tggaggcggg tcccaggtaa    60
agctggagga gtctggg                                                    77
```

<210> SEQ ID NO 5
<211> LENGTH: 28
<212> TYPE: DNA
<213> ORGANISM: Artificial

<220> FEATURE:
<223> OTHER INFORMATION: Reverse primer

<400> SEQUENCE: 5
gaagatctga ggagacggtg acctgggt                                        28

<210> SEQ ID NO 6
<211> LENGTH: 23
<212> TYPE: PRT
<213> ORGANISM: Artificial
<220> FEATURE:
<223> OTHER INFORMATION: synthetic construct

<400> SEQUENCE: 6

Ser Leu Leu Thr Glu Val Glu Thr Pro Ile Arg Asn Glu Trp Gly Cys
1               5                   10                  15

Arg Cys Asn Asp Ser Ser Asp
            20

<210> SEQ ID NO 7
<211> LENGTH: 15
<212> TYPE: DNA
<213> ORGANISM: Artificial
<220> FEATURE:
<223> OTHER INFORMATION: peptide linker

<400> SEQUENCE: 7
ggggsggggs ggggs                                                       15

<210> SEQ ID NO 8
<211> LENGTH: 21
<212> TYPE: PRT
<213> ORGANISM: Artificial
<220> FEATURE:
<223> OTHER INFORMATION: ompA signal peptide

<400> SEQUENCE: 8

Met Lys Lys Thr Ala Ile Ala Ile Ala Val Ala Leu Ala Gly Phe Ala
1               5                   10                  15

Thr Val Ala Gln Ala
            20

<210> SEQ ID NO 9
<211> LENGTH: 20
<212> TYPE: PRT
<213> ORGANISM: Artificial
<220> FEATURE:
<223> OTHER INFORMATION: linker

<400> SEQUENCE: 9

Ala Gly Gln Gly Ser Gly Gly Gly Ser Gly Gly Gly Ser Gly
1               5                   10                  15

Gly Gly Gly Ser
            20

<210> SEQ ID NO 10
<211> LENGTH: 6
<212> TYPE: PRT
<213> ORGANISM: Artificial
<220> FEATURE:
<223> OTHER INFORMATION: His6 tag

<400> SEQUENCE: 10

His His His His His His
1               5

```
<210> SEQ ID NO 11
<211> LENGTH: 5
<212> TYPE: PRT
<213> ORGANISM: Artificial
<220> FEATURE:
<223> OTHER INFORMATION: BSA12 CDR1

<400> SEQUENCE: 11

Asn Tyr Thr Met Ala
1               5

<210> SEQ ID NO 12
<211> LENGTH: 17
<212> TYPE: PRT
<213> ORGANISM: Artificial
<220> FEATURE:
<223> OTHER INFORMATION: BSA12 CDR2

<400> SEQUENCE: 12

Val Val Ser Arg Gly Gly Gly Ala Thr Asp Tyr Ala Asp Ser Val Lys
1               5                   10                  15

Gly

<210> SEQ ID NO 13
<211> LENGTH: 15
<212> TYPE: PRT
<213> ORGANISM: Artificial
<220> FEATURE:
<223> OTHER INFORMATION: BSA12 CDR3

<400> SEQUENCE: 13

Gly Thr Asp Leu Ser Tyr Tyr Tyr Ser Thr Lys Lys Trp Ala Tyr
1               5                   10                  15
```

SCREENING OF PROTEIN CANDIDATES

CROSS-REFERENCE TO RELATED APPLICATIONS

This application is a national entry of International Patent Application PCT/CA2010/001267 filed Aug. 18, 2010 and claims the benefit of U.S. Provisional Patent Application Ser. No. 61/272,119 filed Aug. 18, 2009 and International Patent Application PCT/CA2009/001501 filed Oct. 14, 2009.

FIELD OF THE INVENTION

The present invention relates to screening of protein candidates. More particularly, the invention relates to the screening of expression levels, biophysical properties, and affinities of protein candidates.

BACKGROUND OF THE INVENTION

Expression levels, biophysical properties and biological functions are three key features of an engineered protein. It is a challenge to preserve or improve expression level and biophysical properties of a protein while engineering its biological functions, as any introduced mutation may influence the structure of the protein, and this influence is by far still relatively unpredictable (Honegger et al, 2009).

Screening for protein candidates (PCs) with good expression levels and higher affinities has become more routine. Very high affinity binders are generated in many laboratories (Jonsson et al, 2008) and expression screening has made it possible to estimate the expression levels of a large number of proteins (Kery et al, 2003).

In contrast, engineering biophysical properties is more challenging. Strategies have been designed in all aspects of protein engineering to generate stable PCs. Single domain antibodies (sdAbs) derived from camelid heavy chain antibodies (Hamers-Casterman et al, 1993) are very stable molecules, but introduction of mutations (for humanization and affinity maturation) can lower their stabilities (Saerens et al, 2005). Careful design of libraries can greatly increase the proportion of PCs with good biophysical properties, but these libraries usually still contain significant percentage of proteins that are not satisfactory (Christ et al, 2007). One of the few exceptions is ankyrin repeats: most if not all reported protein binders built on small ankyrin domains seem to have good biophysical properties (Binz et al, 2004; Kohl et al, 2003). For evolving individual PCs, strategies such as molecular evolution based on sequence consensus (Lehmann et al, 2000) and introduction of potentially stabilizing residues (Ewert et al, 2003) have led to more stable proteins. In the selection process, the addition of high temperature (Jespers et al, 2004), extreme pH (Famm et al, 2008) and proteolytic (Ueda et al, 2004) pressures on PCs as well as selection on higher infectivity of phage displaying these PCs (Jespers et al, 2004; (Jespers et al, 2004 et al, 2005) have all led to successful selection of satisfactory binders. Despite these efforts, the challenge of routinely generating stable protein variants remains unmet. Another disadvantage of these approaches is their requirement for a specific molecular display platform, which is not suitable for many proteins.

It is noteworthy that the above approaches usually address only one of the three key features. In addition to the lack of research tools for generating proteins satisfying all aspects, PCs have to be purified in most cases for their characterization. This purification step renders characterization, even for less-challenging affinity screening, rather tedious work. Purifying and characterizing a large number of PCs thus becomes a significant limitation in protein engineering.

Screening methods for either expression levels (Kery et al, 2003), biophysical properties (Niesen et al, 2008; Woestenenk et al, 2003) or affinities (Leonard et al, 2007) are available, but few of the currently known approaches satisfies the requirement of both simplicity and high-throughput. Most such selection methods still require some level of protein purification, which is time-consuming. Additionally, the art-known methods do not allow screening of all key features outlined above.

SUMMARY OF THE INVENTION

The present invention relates to screening of protein candidates. More particularly, the invention relates to the screening of expression levels, biophysical properties, and affinities of protein candidates.

The present invention provides a method for screening of protein candidates, comprising:
  a) providing fusion proteins, each fusion protein comprising one protein candidate and a protein anchor; and
  b) evaluating the expression levels of the protein candidates; or
  c) evaluating the biophysical properties of the protein candidates; or
  d) evaluating the binding kinetics of the protein candidate; or
  e) any combination of steps b) to d) above,
wherein, the protein anchor provides a means of capture of the protein candidates to facilitate evaluation of expression levels, biophysical characteristics and binding kinetics. The protein anchor may accomplish this via binding to a specific coating on a solid surface.

The present invention further provides a method for screening of protein candidates, comprising:
  a) providing fusion proteins, each fusion protein comprising one protein candidate and a protein anchor; and
  b) evaluating the expression levels of the protein candidates by
    i. binding the protein anchor to a specific coating on a solid surface; and
    ii. measuring the amount of bound fusion proteins; or
  c) evaluating the biophysical properties of the protein candidates by
    i. denaturing the fusion proteins;
    ii. allowing the denatured fusion proteins to refold;
    iii. filtering sample containing the refolded fusion proteins;
    iv. binding the protein anchor to a specific coating on a solid surface;
    v. measuring the amount of bound fusion proteins; and
    vi. comparing the amount of bound fusion proteins to that obtained in step b); or
  d) evaluating the binding kinetics of the protein candidate by
    i. binding the protein anchor to a specific coating on a solid surface; and
    ii. measuring the binding kinetics of the protein candidates to their target/antigen by allowing the target/antigen to bind to the protein candidates and observing their associations and dissociations; or
  e) any combination of steps b) to d) above.

In the method as described above, each of the three screening modules (steps b) to d)) may be performed independently, in parallel or in succession. The method as described generally does not require purification of the fusion proteins or protein candidates.

In the method described above, the expression levels may be measured by ELISA; the denaturation may be accomplished by exposure to heat or extreme pH; and/or the binding kinetics may be measured by surface plasmon resonance.

The present invention is also directed to fusion proteins comprising a protein anchor and protein candidates. The protein anchor may comprise an antibody or antibody fragment comprising a complementarity determining region (CDR) 1 sequence of NYTMA (SEQ ID NO:11); a CDR2 sequence of VVSRGGGATDYADSVKG (SEQ ID NO:12); and a CDR3 sequence of GTDLSYYYSTKKWAY (SEQ ID NO:13); the antibody or fragment thereof may be based on BSA12 (SEQ ID NOs: 1 and 2), or may comprise BSA12 itself, and the protein candidates (PCs) may be any suitable proteins for screening. In these cases, the specific coating is bovine serum albumin.

The present invention further provides a vector for expressing the fusion proteins described above, as well as a precursor vector into which the nucleic acid molecule encoding the protein candidate is cloned. In one non-limiting example, the precursor vector is pBSA12 (FIG. 1, SEQ ID NO. 3).

An approach for fast screening of expression, biophysical-properties and affinities, which allows the screening of a large number of PCs at the early stage of protein engineering to exclude or greatly reduce the number of unsatisfactory candidates, is described herein. This approach also allows the ranking of the PCs by their dissociation rates, which are usually closely related to their affinities, without protein purification. In one embodiment, the PCs are fused to a camelid sdAb BSA12 (Li et al, 2009), which is very stable and has an extreme affinity to BSA yet this interaction can be completely disrupted by low pH. The affinity of the sdAb BSA12 anchors onto any BSA-coated surface and greatly contributed to the simplicity of the presently described method and the accuracy of the generated data.

Another advantage of the present method is that it does not rely on ligand binding for the selection of good biophysical properties, which can broaden its application to practically any area of protein engineering. For example, the present method may assist in selecting enzyme candidates with higher stabilities, or identifying optimum refolding conditions for various proteins. The high throughput feature of the present approach also allows for the selection of a very large number of PCs to analyze contributions of various residues to solubility and stability, and to identify residues with positive contributions to a more stable structure. As the evidence of protein folding has become obvious in the development of diseases such as Alzheimer's diseases and Parkinson's disease, this approach also allows for investigation of misfolding mechanisms and searching for peptidic drug candidates to prevent the formation of protein aggregates.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 3A depicts the PC-BSA12 concentrations of 10 out of the approximately 190 constructs in cell-conditioned media as measured by ELISA on BSA. Background reading with no BSA coating was subtracted from the original data. FIG. 3B is a Western blot of cell-conditioned media of the 10 sdAb-BSA12 clones. FIG. 3C is a Western blot of pellets (P) and supernatants (S) of six of the sdAbs when expressed as monomers.

FIG. 4A depicts the concentrations of 18 PC-BSA12s as measured by ELISA on BSA with (60° C. or 80° C.) or without (RT) heating and subsequent filtration of the samples. Three clones having significant signal reduction after heating and filtration, marked by "x", and three without, marked by "*", were selected for further analysis. FIG. 4B shows SEC profiles of BSA12 and four sdAbs. Elution positions of protein standards BSA (67 kDa), ovalalbumin (43 kDa), chymotrypsinogen, (25 kDa) and ribonuclease (13.7 kDa) are indicated above the graphs. FIG. 4C shows circular dichroism spectra of purified BSA12 and four sdAbs in 10 mM phosphate buffer, pH 7.0. FIG. 4D shows graphs tracking heat-induced denaturation of BSA12 and three sdAbs as measured by CD at 218 nm.

FIG. 5A shows normalized sensorgram overlays in dissociation phase of Fc binding to Fc17-BSA12 of 27 independent transformants. FIG. 5B shows the correlation between amounts of Fc17-BSA12 captured and amounts of Fc bound to Fc17. FIG. 5C depicts the amount of 51 sdAb-BSA12 fusions and BSA12 captured on immobilized BSA. The dashed line represents the level of BSA12 captured in flow cell 1 in the first round. FIG. 5D is normalized sensorgram overlays in dissociation phase of free Fc bindings to 43 sdAb-BSA12s representing 12 different sdAb-BSA12 clones. Those of Fc7-BSA12, Fc12-BSA12 and FC75-BSA12 are shown in thick solid, dotted and dashed lines, respectively. FIG. 5E is sensorgram overlays of purified Fc7, Fc12 and Fc75 binding to immobilized Fc.

DETAILED DESCRIPTION OF THE INVENTION

The present invention relates to screening of protein candidates. More particularly, the invention relates to the screening of expression levels, biophysical properties, and affinities of protein candidates.

The present invention provides a method for screening of protein candidates, comprising:
a) providing fusion proteins, each fusion protein comprising one protein candidates and a protein anchor; and
b) evaluating the expression levels of the protein candidates; or
c) evaluating the biophysical properties of the protein candidates; or
d) evaluating the binding kinetics of the protein candidate; or
e) any combination of steps b) to d) above.

In the method as just described, the protein anchor provides a means of capture of the protein candidates to a specific coating to facilitate evaluation of expression levels, biophysical characteristics and binding kinetics. The protein anchor may accomplish this via binding to a specific coating on a solid surface.

More specifically, the present invention provides a method for screening of protein candidates, comprising:
a) providing fusion proteins, each fusion protein comprising one protein candidates and a protein anchor; and
b) evaluating the expression levels of the protein candidates by
  i. binding the protein anchor to a specific coating on a solid surface; and
  ii. measuring the amount of bound fusion proteins; or
c) evaluating the biophysical properties of the protein candidates by
  i. denaturing the fusion proteins;
  ii. allowing the denatured fusion proteins to refold;
  iii. filtering sample containing the refolded fusion proteins;
  iv. binding the protein anchor to a specific coating on a solid surface;
  v. measuring the amount of bound fusion proteins; and
  vi. comparing the amount of bound fusion proteins to that obtained in step b); or
d) evaluating the binding kinetics of the protein candidate by
  i. binding the protein anchor to a specific coating on a solid surface; and
  ii. measuring the binding kinetics of the protein candidates to their target/antigen by allowing the target/antigen to bind to the protein candidates and observing their associations and dissociations; or
e) any combination of steps b) to d) above.

Figure 2:
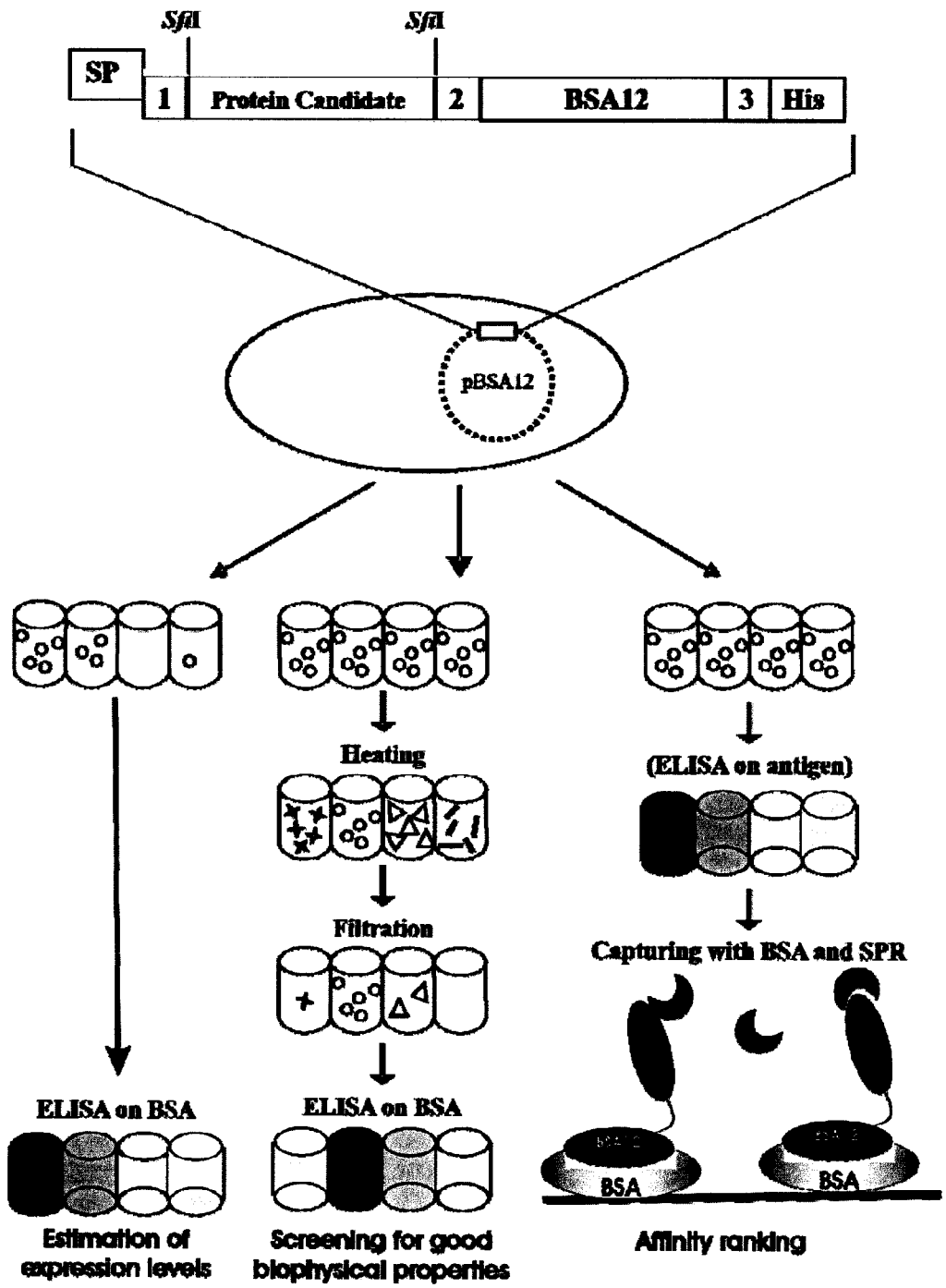
FIG. 2 is a schematic representation of fast screening of expression-levels, biophysical properties and affinities of PCs, using one embodiment of the present invention. PCs to be screened are fused directly to a protein anchor (BSA12) by cloning into a vector (pBSA12) to make a sub-library. Cell lysates or cell-conditioned media of individual clones are used to estimate the expression of PC-BSA12 (left panel) and screen for binders with good biophysical properties (the middle panel) as described in the text. For ranking affinities of the PCs, the same samples are captured onto an SPR chip surface pre-immobilized with BSA, and the antigen is injected to measure its binding to the PCs (right panel). ELISA on antigen to pre-screen binders is optional. SP, ompA signal peptide (MKKTAIAIAVALAGFATVAQA; SEQ ID NO:8); L, linker (AGQGSGGGSGGGGSGGGGS; SEQ ID NO:9); and His, histidine purification tag (HHHHHH; SEQ ID NO:10).

The method as described herein is designed to provide information on expression levels, biophysical properties and affinities of a large number of PCs without requiring purification of such molecules (FIG. 2). Each of the three screening modules (steps b) to d)) may be performed independently, in parallel or in succession.

The method of the present invention allows rapid screening of protein candidates (PCs). A "protein candidate" may be any suitable protein of interest, regardless of its eventual application. The protein candidates may be based on a naturally-occurring protein, or may be an engineered protein; the libraries of protein candidates for screening may be obtained by any method known in the art, for example, but not limited to phage-display, ribosome display, yeast display, affinity maturation, genomic DNA, cDNA or mutation libraries.

In order to screen the PCs using the method of the present invention, the PCs are provided as fusion proteins. The fusion protein may comprise a protein candidate and a protein anchor. As described above, the protein candidate is the protein of interest; the "protein anchor" is a protein that provides known characteristics to the fusion protein, and it allows for the capture of the fusion protein. In order to be useful in the method of the present invention, the protein anchor should:

1) have very high affinity to its target or antigen. For example, and without wishing to be limiting, the protein anchor may have a $K_D$ below about 10 pM; a protein anchor with a $K_D$ over about 100 pm would start to cause a drifting baseline in $k_d$ ranking experiments, and therefore would affect the accuracy of collected data and doesn't allow ranking of binders with very high affinities in the presently described method. Therefore, in a specific, non-limiting example, the protein anchor may have a $K_D$ below about 100 pm, or below about 10 pm;

2) have an interaction with its target or antigen that may be easily disrupted despite its high affinity. The disruption of the interaction between protein anchor and target may be disrupted by any suitable method, for example but not limited to changes in pH, changes in salt concentration, or changes in buffer;

3) exist in monomeric form and have high thermostability. This can be measured by size exclusion chromatography (for its monomer form determination) or circular dichroism at various temperatures (for its thermal denaturation curve). Preferably the melting temperature of the anchor protein is higher than 65° C.;

4) show little non-specific bindings to other targets, antigens, or proteins in general (i.e., is highly specific to its target); or 5) any combination of 1) to 4).

Additionally, the target/antigen to which the protein anchor binds should be resistant to the reagent that interrupts the protein anchor interaction with the target/antigen.

As described herein, the protein anchor will allow the characteristics of the fusion protein, and thus the protein candidate, to be evaluated without relying on the properties of the protein candidate.

The protein anchor may be any suitable protein possessing the characteristic 1) to 5), as described above. The protein anchor may be an antibody or antibody fragment, an enzyme, a structural protein, or any other suitable type of protein. In one non-limiting example, the protein anchor may be an antibody or antibody fragment comprising a complementarity determining region (CDR) 1 sequence of NYTMA (SEQ ID NO:11); a CDR2 sequence of VVS-RGGGATDYADSVKG (SEQ ID NO:12); and a CDR3 sequence of GTDLSYYYSTKKWAY (SEQ ID NO:13). In another specific, non-limiting example, the protein anchor may be an antibody or antibody fragment based on BSA12, or may comprise BSA12 itself (SEQ ID NO:2; as described in PCT/US2009/60495; also in WO 2010/043057) or a mutant or fragment thereof. In the case where BSA12 or an antibody based thereon is used as the protein anchor, the target or antigen will be bovine serum albumin (BSA). In another non-limiting example, the protein anchor may be the affibodies binding to serum albumin (Jonsson et al, 2008).

The fusion protein may additionally comprise additional sequences to aid in expression, detection or purification of a recombinant antibody or fragment thereof. For example, and without wishing to be limiting, the antibody or fragment thereof may comprise a targeting or signal sequence (for example, but not limited to ompA), a detection tag (for example, but not limited to c-Myc), a purification tag (for example, but not limited to a histidine purification tag), or a combination thereof.

The expression levels of the protein candidates may be evaluated by binding the protein anchor of the fusion proteins to a specific coating on a solid surface and measuring the amount of bound fusion proteins. The specific coating may comprise the target or antigen to which the protein anchor binds. Thus, the protein anchor may bind to the specific coating on the solid surface and the fusion protein may be immobilized on the solid surface. The solid surface may be any suitable surface, for example, but not limited to the well surface of a microtiter plate, channels of surface plasmon resonance (SPR) sensorchips, membranes etc. The amount of the fusion protein on the solid surface may then be measured by any suitable method, for example, but not limited to ELISA, SPR, dot blots, Western blots or protein microarray technologies. As shown in the examples, the level of expression of the fusion protein is a reliable indicator of the expression level of the protein candidate alone.

The biophysical properties of the protein candidate may be evaluated by denaturing the fusion protein and allowing it to refold, then binding the protein anchor of the fusion protein to a specific coating on a solid surface and measuring the concentration of fusion protein. The fusion protein may be denatured by any suitable method. For example, but without wishing to be limiting in any manner, the fusion protein may be denatured by exposure to heat or to extreme pH. In a non-limiting example, the heat may be temperatures in the range of about 60 to about 90° C.; for example, the denaturing temperature may be about 60, 65, 70, 75, 80, 85, or 90° C., or any temperature therebetween, or any range of temperature defined by any two values just recited. In another non-limiting example, the extreme pH may be in the range of about pH 3.5 to about pH 1 (about 3.5 3.0, 2.5, 2.0, 1.5, or 1.0, or any pH therebetween, or any range of pH defined by any two values just recited) or about pH 9.5 to about pH 12 (about 9.5 10, 10.5, 11.0, 11.5, or 12.0, or any pH therebetween, or any range of pH defined by any two values just recited). In order to allow the fusion protein to refold, the temperature and/or pH may be returned to more normal value. The refolded fusion protein may be filtered using any suitable method; for example, and without wishing to be limiting in any manner, the refolded fusion protein may be filtered using a membrane filter. Without wishing to be bound by theory, protein candidates with undesirable biophysical properties (for example, but not limited to low stability, low solubility, oligomerization) will be removed from solution either by precipitation or by filtration. The refolded fusion protein is then bound to a specific coating on a solid surface by its protein anchor portion and the concentration of refolded fusion protein is measured. The concentration of refolded fusion protein may then be compared to that observed in the step of evaluating protein expression levels (step b)). If the two concentrations of a fusion protein (with and without denaturation and filtration) are similar, then the fusion protein may said to possess good biophysical properties. As shown in the examples, the biophysical properties of the fusion protein are a relatively good indicator of the biophysical properties of the protein candidate alone.

The binding kinetics of the protein candidates may be evaluated by binding the protein anchor of the fusion protein to a specific coating on a solid surface such as, but not limited to the sensorchips of a machine which measures surface plasmon resonance (SPR), and measuring the binding kinetics of fusion proteins to their targets/antigens. The binding kinetics may be measured using any suitable technology, for example but not limited to SPR. Once the fusion protein is captured on the solid surface, the ligand that is bound by the PCs may be used to measure the PC binding kinetics, for example, but not limited to $K_D$, off-rate, etc.

As would be understood by a person of skill in the art, the method of the present invention may be put into practice using various technologies. In one embodiment of the present invention, DNA encoding PCs is first amplified by PCR and cloned into a vector pBSA12 to generate a sub-library of PC-BSA12 fusions. Individual clones from this sub-library may be grown in microtiter plates, and supernatants of cell lysates containing expressed PC-BSA12s can be used for all three screenings. The amount of PC-BSA12s secreted into the growth media was presently found sufficient to perform the experiments, and was therefore used. Expression level was estimated by ELISA on BSA. In the excess of BSA coated on microtiter plates and due to the very high affinity of BSA12 to BSA ($K_D$=4 pM; Li et al, 2009), expression levels of PC-BSA12s can be estimated by measuring the amount of PC-BSA12 bound to BSA (FIG. 2, left panel). Screening of PCs with good biophysical properties was conducted in the same way, except that the samples are heated and filtered prior to performing ELISA. Those PCs that give similar ELISA results before and after heating were considered to have good biophysical properties (FIG. 2, middle panel). If binding of the PCs to their target is of interest, the same supernatant samples can be used to rank the PCs' affinities. To rank the affinity of protein candidates, BSA may first be mobilized on an SPR sensorchip surface, and a sample containing PC-BSA12s can be flowed over the chip to capture PC-BSA12s. The target antigen is lastly injected to measure its affinity to the binders. The BSA12 chip surface is then regenerated and can be reused for another round of screening (FIG. 2, right panel).

The present invention is also directed to a fusion protein comprising a protein anchor and a protein candidate. The protein anchor may be as described above. In a specific, non-limiting example, the protein anchor may be an antibody or antibody fragment comprising a complementarity determining region (CDR) 1 sequence of NYTMA (SEQ ID NO:11); a CDR2 sequence of VVSRGGGATDYADSVKG (SEQ ID NO:12); and a CDR3 sequence of GTDLSYYYST-KKWAY (SEQ ID NO:13); the protein anchor may be an antibody or antibody fragment based on BSA12, or may comprise BSA12 itself or a mutant thereof, and the protein candidate may be any suitable protein for screening.

The present invention further provides a vector for expressing the fusion proteins described above, as well as a precursor vector into which the nucleic acid molecule encoding the protein candidate is cloned. In one non-limiting example, the precursor vector is pBSA12.

The presently described approach for fast screening of expression, biophysical-properties and affinities allows for screening of a large number of PCs at the early stages of protein engineering. Not only does the present method contribute to reducing the number of unsatisfactory candidates, but this approach also allows the ranking of the PC affinities without protein purification. Another advantage of the present method is that it is independent of ligand binding for the selection of good biophysical properties, which can broaden its application to numerous areas of protein engineering. The high throughput feature of the present approach also allows for the selection of a very large number of PCs, not only to analyze contributions of various residues to solubility and stability, but also to identify residues with positive contributions to a more stable structure.

The present invention will be further illustrated in the following examples. However, it is to be understood that these examples are for illustrative purposes only and should not be used to limit the scope of the present invention in any manner.

Example 1 pBAS12 Vector Construction

A vector was constructed to assist in expressing fusion proteins comprising a protein candidate fused to BSA12.

Briefly, DNA encoding BSA12 (Li et al, 2009) was amplified using primers:

```
                         (Forward primer; SEQ ID NO: 4)
CGGGATCCGGTGGAGGCGGGTCCGGTGGAGGCGGGTCCGGTGGAGGCGG

GTCCCAGGTAAAGCTGGAGGAGTCTGGG;

(Reverse primer; SEQ ID NO: 5)
GAAGATCTGAGGAGACGGTGACCTGGGT;
```

Figure 1:
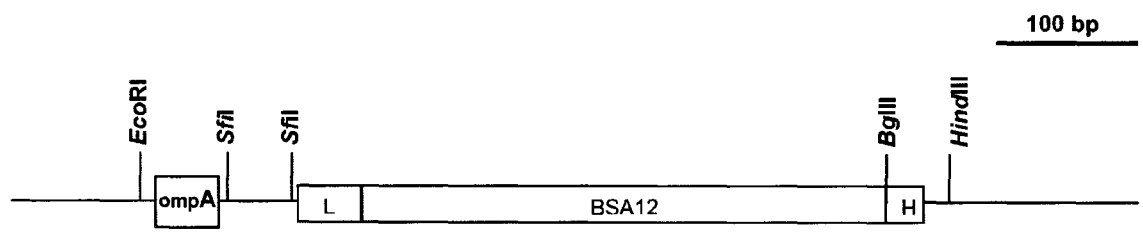
FIG. 1 is a schematic presentation of the vector pBSA12. The ompA leader sequence (ompA) will be removed during secretion. SfiI restriction sites are usually used to fuse protein candidates with BSA12 linked with the linker (L) sequence. The 6× Histidine tag (H) is designed for purification of PC-BSA12s by immobilized metal affinity chromatography.

The PCR product, after digestion with BamHI and ApaI, was inserted into pMED2, a slight modification of an E. coli expression vector pSJF2 (Tanha et al, 2003), generating a new vector pBSA12 (FIG. 1, SEQ ID NO. 3), which facilitates fusion of other proteins to BSA12.

Example 2

Phage Panning and Cloning of Protein Candidates

A human $V_H$ sdAb phage display library (kindly provided by Dr. J. Tanha, NRC, Canada) was employed to distinguish clones with reasonable and poor expressions in E. coli. This library was built on the framework of a stable human $V_H$ (To et al, 2005) but was found to display many low-expressing and aggregate-prone binders (Arbabi-Ghahroudi et al, 2009a). The protein antigen used for biopanning was the ectodomain of matrix protein 2 of human influenza virus A (M2e, SLLTEVETPIRNEWGCRCNDSSD (SEQ ID NO:6); which was synthesized and purified to over 90% purity by Genescript (Piscataway, N.J.). Phage display biopanning was generally conducted as previously described (Arbabi-Ghahroudi et al, 2009b), with the biopanning rounds reduced from four to two. Phage ELISA was performed with a small number of individual phage eluted from each round, usually 20-50, to estimate the percentage of phage clones binding to the antigens, and the eluted phage having larger than 50% positive clones were chosen for the construction of sub-libraries of sdAb-BSA12s. This established the library to be screened by the method of the present invention.

After the two rounds of biopanning on the M2e peptide antigen, DNA encoding the sdAbs was amplified from the eluted phage and cloned into vector pBSA12, described in Example 1. DNA encoding PCs was first amplified by PCR and cloned into the pBSA12 vector to generate a sub-library of sdAb-BSA12 fusions. DNA encoding potential binders was amplified with the addition of SfiI restriction sites to both ends of the fragment and DNA encoding a peptide linker GGGGSGGGGSGGGGS (SEQ ID NO:7) at the 3'-end. The PCR fragments were inserted into pBSA12. The cloning procedure resulted in over 90 percent, often close to 100 percent, of individual clones harbouring a binder gene (results not shown).

Example 3

Fusion Protein Expression

Individual clones from the sub-library established in Example 2 were grown in microtiter plates, and supernatants of cell lysates containing expressed sdAb-BSA12s can be used for all three screenings. Alternatively, as in the present example, fusion protein secreted into the growth media may be sufficient to perform the experiments.

Briefly, individual sdAb-BSA12 clones were inoculated in LB medium, supplemented with 100 µg/ml ampicillin, in 96-well microtiter plates and grown at 37° C. overnight with shaking. Cell-conditioned media were collected after centrifugation of the cell cultures. (When supernatant of cell lysates are to be used, the cell pellets may be lysed by adding CelLytic B (Sigma, St. Louis, Mo.) according to product instructions and supernatants of cell lysates may be collected after centrifugation. Other methods of obtaining the supernatants of cell lysates may also be used.)

Example 4

Assessing Protein Candidate Expression

The expression levels of the protein candidates were evaluated. To do so, the cell-conditioned media obtained in Example 3 was submitted to ELISA experiments.

Briefly, the cell-conditioned media of about 190 clones were used to perform ELISA using BSA as the antigen. 10 µg/ml of antigens, either BSA or target of the binders, were coated onto microtiter plates for overnight at 4° C. in 15 mM $Na_2CO_3$, pH9.6.2% skim milk in PBS was added to the wells to block non-specific binding. 50 µl of the above-collected samples, either cell-conditioned medium or cell lysate supernatants, were added to the wells and incubated for 1 hr at 37° C. Bound proteins were detected by HRP-labelled anti-His tag antibody using standard ELISA procedure.

Some of the collected samples were separated by SDS-PAGE, and His-tagged proteins were detected by Western blot using goat anti-llama and alkaline phosphotase-labelled rabbit anti-goat antibody (Cedarlane, Burlington, ON).

Figure 3:
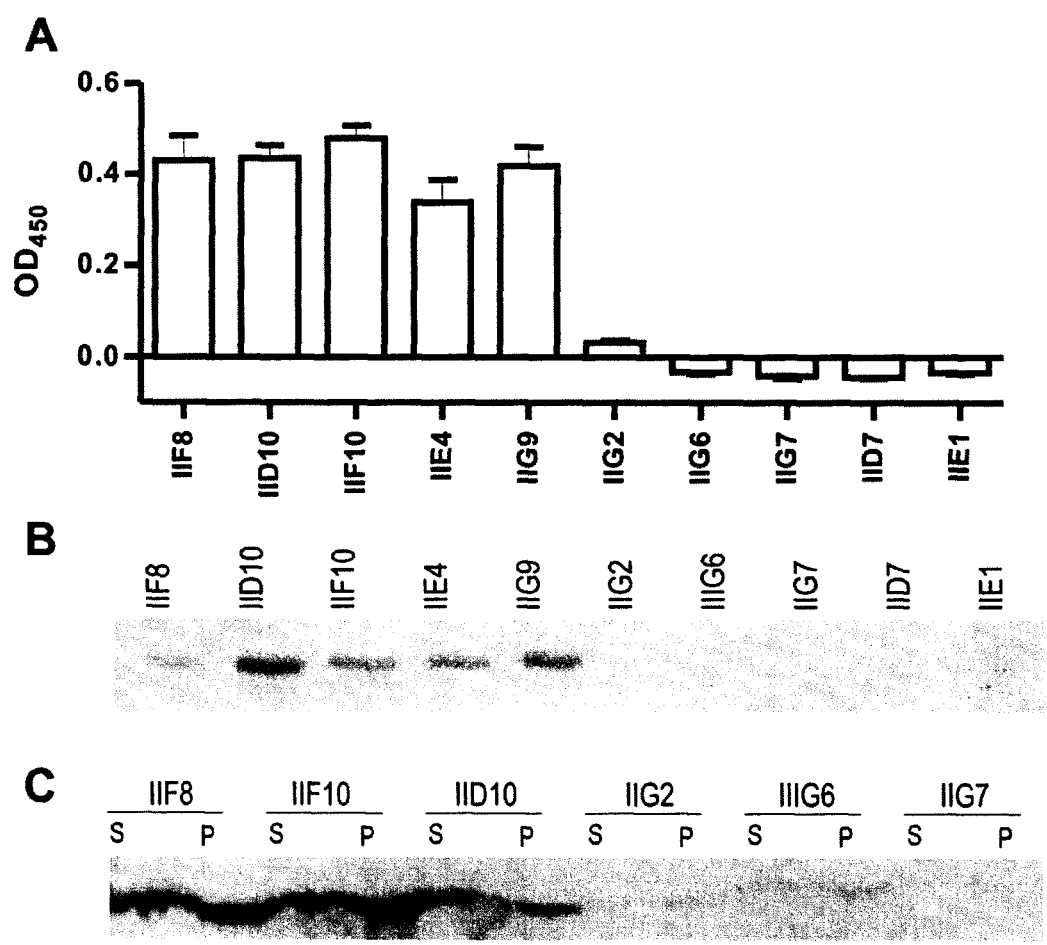
FIG. 3 shows results of screening of expression levels of PCs.

About 90% of the clones had no detectable expression of the fusion proteins. ELISA (FIG. 3A) and Western blots (FIG. 3B) representing 10 of the 190 clones (five with reasonable and five with poor expressions) are presented. Without wishing to be bound by theory, the very high affinity of BSA12 to BSA may allow near-complete capture of sdAb-BSA12 fusion proteins, which can resist stringent washes. Advantageously, this approach makes the capture of sdAbs independent of their other features, such as affinities to ligands, solubility and stability. The ELISA reading is therefore only dependent on the concentration of sdAb-BSA12s in the solutions, and may provide a more accurate estimation of the expression levels than prior art methods.

To investigate whether the expression levels of sdAb-BSA12 fusions reflect those of the sdAbs when expressed alone, three sdAbs with reasonable expression (IIA11, IIG3 and IIG9) and three with poor expression (IID3, IID4 and IIF10), when expressed as BSA-fusions, were cloned to express the sdAbs. DNA encoding these six human sdAbs were cloned into the E. coli expression vector pMED2.

Clones were then inoculated in 25 ml LB with 200 µg/ml ampicillin and incubated at 37° C. with 200 rpm shaking overnight. 20 ml of the culture was used to inoculate 1 L of M9 medium (0.2% glucose, 0.6% $Na_2HPO_4$, 0.3% $KH_2PO_4$, 0.1% NH$_4$Cl, 0.05% NaCl, 1 mM MgCl$_2$, 0.1 mM CaCl$_2$) supplemented with 0.4% casamino acids, 5 mg/l of vitamin B1 and 200 µg/ml Ampicillin, and cultured for 24 hrs. 100 ml of 10×TB nutrients (12% Tryptone, 24% yeast extract and 4% glycerol), 2 ml of 100 mg/ml ampicillin and 1 ml of 1 M isopropyl-beta-D-Thiogalactopyranoside (IPTG) were added to the culture and incubation was continued for another 65-70 hr at 28° C. with 200 rpm shaking. E. coli cells were harvested by centrifugation and lysed with lysozyme to release the sdAbs, which were expressed periplasmically. Cell lysates were centrifuged, and supernatants were loaded onto High-Trap™ chelating affinity columns (GE Healthcare, Baie d'Urfé, QC). After washing the columns with four column volume of 50 mM Tris, 25 mM NaCl, pH7.4, His-tagged proteins were eluted with a linear gradient (2.5 to 500 mM) of immidazole, and the eluted proteins were dialyzed in PBS buffer.

The results (FIG. 3C) demonstrated that expression levels of sdAb-BSA12 fusions were good indicators of the expression of the sdAbs. This suggests that fusion of PCs to BSA12 and estimation of the expression levels of such fusions provide an easy approach to screen a large number of PCs for their expression levels.

Example 5

Assessing Protein Candidate Biophysical Properties

BSA12 has a relatively high thermostability with a T$_m$ of ~70° C. (see FIG. 4D). Based on the hypothesis that less stable proteins would form aggregates upon heating and the aggregates can be filtrated out, performing ELISA with denatured and non-denatured samples would allow the evaluation of biological properties.

For non-denatured samples, ELISA was performed as described in Example 4. For the denatured samples, cell-conditioned media of 18 sdAb-BSA12 clones with reasonable expression, as determined in Example 4, were heated (60° C. and 80° C., 5 min) and filtered before being used for ELISA on BSA. The sdAb-BSA12 clones were expressed as described in Example 3. 60 µl cell-conditioned medium was transferred to PCR tubes, and the samples were heated at either 60° C. or 80° C. for 5 min on a GeneAmp PCR system 9700 (Applied Biosystems, Foster City, Calif.) and allowed to slowly cool to room temperature. The samples were then transferred to a Multi-Well Filter Plates (Pall Coorportions, Ann Arbor, Mich.) and centrifuged (4000 rpm, 30 min), and the flow-through were collected. ELISA studies were then performed as described in Example 4.

Figure 4:
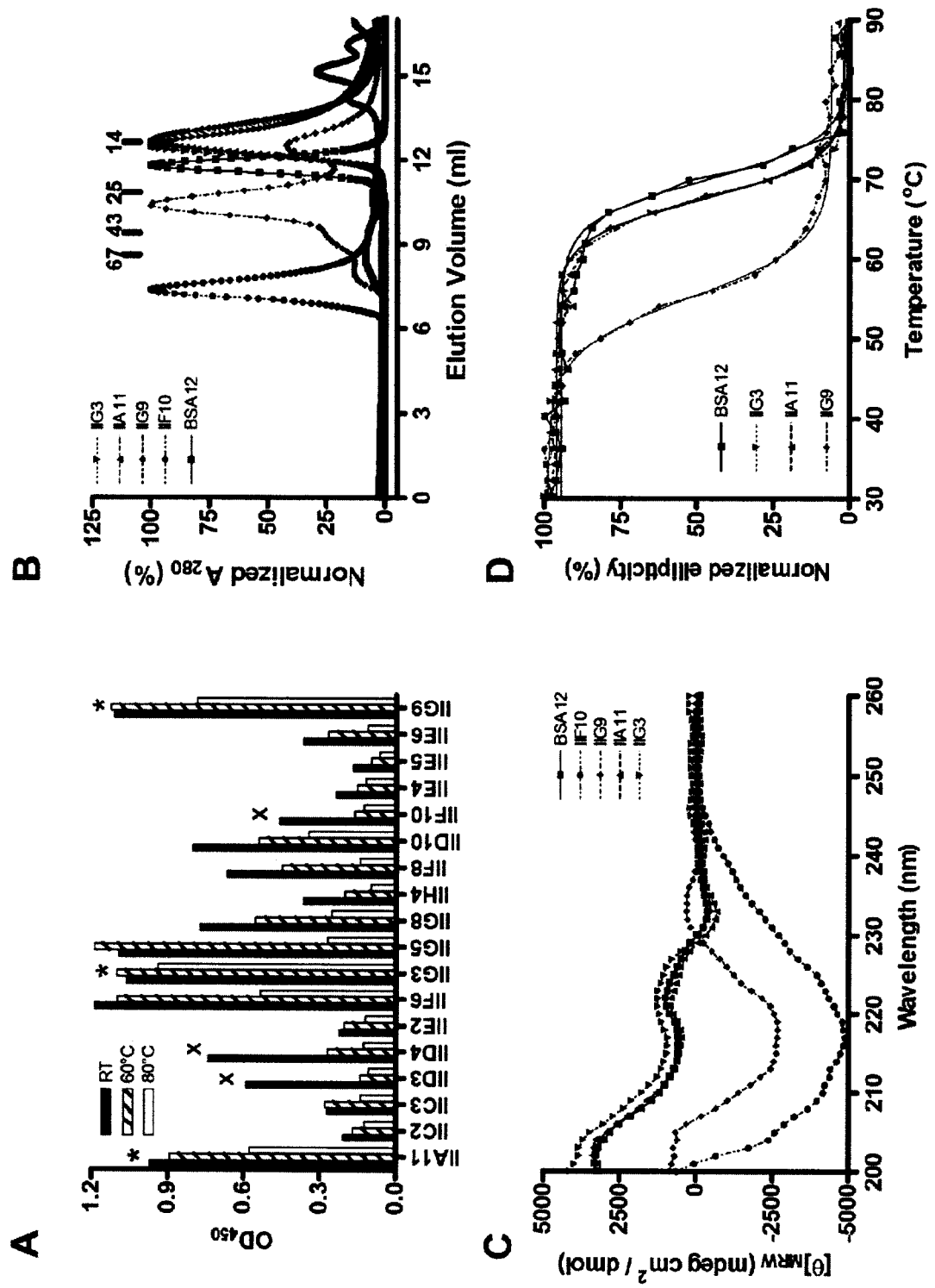
FIG. 4 shows results of screening of biophysical properties.

When compared to samples processed without the heating and filtration steps, a significant reduction in ELISA signals in some samples was observed, whereas little change was seen in others (FIG. 4A). This suggested that those sdAb-BSA12 samples behaving similarly before and after heating can either resist heat denaturation or refold rapidly after heating is stopped—a clear indication of good biophysical properties.

To evaluate whether the characteristics of the fusion protein are indicative of the protein candidate characteristics, three heat-resistant (IIA11, IIG3, IIG9) and three heat-sensitive sdAbs (IID3, IID4 and IIF10) when fused to BSA12, were expressed as monomeric proteins. Cloning, expression and purification of the sdAbs was performed as described in Example 4. Yields of the heat-resistant sdAbs IIG3, IIG9 and IIA11 are 6.0, 2.0 and 1.5 mg/L of culture, respectively. Relatively pure protein was obtained from only one of the three heat-sensitive sdAbs (IIF10), with a yield of 3 mg/L of culture; purification of the other two heat-sensitive sdAbs failed in repeated efforts.

The four isolated sdAbs and BSA12 were analyzed by size exclusion chromatography (SEC) to determine whether they form oligomers or aggregates (FIG. 4B). Separations were carried out in 10 mM HEPES, pH 7.4, containing 150 mM NaCl, 3.4 mM EDTA and 0.05% Tween 20 on Superdex 75 (GE Healthcare) SEC on an ÄKTA FPLC system (GE Healthcare). Protein standards (GE Healthcare) were run under the same conditions.

BSA12 exists as monomer on a Supderdex75™ column with a measured molecular mass (MMM) of 18 kDa (elution volume at 11.8 ml). Similar profiles were observed from two of the three heat-resistant human sdAbs, IIG3 and IIA11 with a MMM of 13.7 kDa (elution volume at 12.5 ml) and 12.7 kDa (elution volume at 12.7 ml), respectively. These MMMs are very similar to their calculated MW of ~13 kDa. No aggregation was observed from IIG3, and a small aggregation bump at elution volume of 7.5-10 ml can be seen for IIA11. The third heat-resistant sdAb IIG9 has a major elution peak (10.4 ml), a minor elution peak (12.5 ml) and some shoulders in the range of 7 and 10 ml. This suggests that the majority of IIG9 exists as a dimer with a MMM of 31.7 kDa, but monomeric (MMM=13.7) and higher-valency oligomeric protein complex also exist. The only heat-sensitive human sdAb purified (IIF10) had a major peak at 7.4 ml representing protein complexes of five sdAbs or higher; some minor peaks were also observed, which may represent contamination of unwanted proteins in the preparation, based on their elution volumes.

The CD spectra (FIG. 4C) of the sdAbs were determined using a circular dichroism (CD) spectrometer. To provide substantially pure protein for CD, the proteins were collected at their major SEC peaks for BSA12, IIA3, IIG9 and IIF10 and at the 10.4 ml (dimer) and 12.5 ml (monomer) peaks for IIG9. Briefly, proteins were separated in a Superdex75 SEC in 10 mM phosphate buffer, pH 7.0, and peaks representing major formats of proteins were collected and used in CD analysis. CD from 250 to 200 nm was measured with the protein concentrations of ~2.5 µM in a 10 mm path-length cuvette with a J-850 CD spectrometer (JASCO). Data were collected at a band width of 1.0 nm and scanning speed of 50 nm/min with two data accumulations and subtracted with buffer control. Molar ellipiticity was calculated as previously described (Schmid, 1997); above parameters, with the exception of only one accumulation, were used in determining thermal denaturation of proteins, which was measured at every two degrees from 30 to 90° C. at a temperature shift speed of 1° C./min. CD values at 218 nm were plotted to temperature in GraphPadPrism and Boltzmann Sigmoidal modal was used to calculate the T$_m$ of the proteins.

IIG3 and IIA11 have similar CD spectrometry profiles, which in turn are similar to that of BSA12. For IIG9, which exists as a mixture of monomer, dimer and other oligomers, the monomeric portion and dimeric peaks were analyzed separately; their CD profiles were found nearly identical (only that of the monomeric peak is shown in FIG. 4C). This CD profile is different from those of BSA12, IIG3 and IIA11, which all exist mainly as monomeric proteins. The CD spectrum also suggested that IIG9 has a significantly higher portion of α-helices, which is usually not seen in variable domains of antibodies. The CD spectrum of IIF10 suggested that it has an even higher proportion of α-helices.

To better evaluate protein stability, temperature-induced denaturation of the proteins was also investigated using CD (FIG. 4D) as described above. Plotting CD values of BSA12 at 218 nm gave a calculated $T_m$ of 70° C., inline with camelid sdAbs reported by others (Dumoulin et al, 2002). The two monomeric heat-resistant human sdAbs, IIA3 and IIG11, have a $T_m$ of 68° C. The third human sdAb IIG9, which exists in multiple forms (FIG. 4B), selected by the heating process has a much lower $T_m$ of 55° C. Interestingly, the CD spectrum of the only available heat-sensitive human sdAb, IIF10, showed little change during heating (data not shown). Without wishing to be bound by theory, possible explanations include: the IIF10 aggregates provide an ultra-stable structure, or the CD spectrum (FIG. 4C) represents an unstructured format.

An effort was made to distinguish proteins with good biophysical properties from those with less desirable properties using ELISA. One of the three heat-resistant sdAbs exists as pure monomer, the second predominantly as monomer and the third as a mixture of dimer, monomer and other type of oligomers. In contrast, the only heat sensitive sdAb obtained exists mainly, if not entirely, as aggregates. Despite the fact that one of the three heat-resistant sdAbs did not meet the biophysical property standards set, the screening method is still regarded as very useful as it excluded most PCs with unsatisfactory features. Notably, little protein was obtained from two of the three clones that were sensitive to heat treatment, even though expression screening suggested that they would express reasonably well. It is not unusual that scaling-up of protein expression leads to poor yields for some proteins. The benefit to the present method is its ability to screen these clones out.

Example 6

Assessing Protein Candidate Binding Kinetics

If the PCs are also potential binders, their binding kinetics can be investigated using cell-conditioned media or cell lysates containing PC-BSA12s. Since the majority of human sdAbs obtained from the M2e biopanning had poor expression in *E. coli*, this portion of the present method was evaluated using an anti-human IgG1 llama sdAb library. As camelid sdAbs are known to have very good stability in general, use of this library would allow analysis of affinities of a large number of binders without consideration of their expression and stability.

An immune llama sdAb library was constructed after a llama was immunized with human IgG and other antigens, as previously described (Li et al, 2009). After two rounds of biopanning, a sub-library of llama sdAb-BSA12s was constructed and cell-conditioned media were used to study the dissociation of potential binders.

The binding kinetics of human Fc to llama sdAb-BSA12s captured on immobilized BSA were determined by SPR using Biacore 3000 (GE Healthcare). Approximately 8000 RUs of BSA were immobilized on research grade Sensorchip CM5 (GE Healthcare). Immobilizations were carried out at a protein concentration of 50 µg/ml in 10 mM acetate buffer, pH4.5, using amine coupling kit supplied by the manufacturer. Typically 40 µl of culture supernatants were added to 96 well-microtiter plates manually and covered by self-adhesive foils (GE Healthcare). 60 µl of the running buffer was added to the wells to dilute culture supernatants. 40 µl of the diluted culture supernatants were then injected to flow cells 2, 3 & 4 alternatively at a flow rate of 5 µl/min. For the reference surface, 20 µl of 80 nM BSA12 was injected to flow cell 1. 60 µl of buffer blank and then 1 µM human Fc was injected over all 4 flow cells at a flow rate of 20 µl/min and the dissociations were monitored for 3 min followed by surface regeneration with 15 injection of 10 mM Glycine/HCl pH 2.0. The same BSA surfaces were repeatedly used to collect all data sets. In all instances, analyses were carried out at 25° C. in 10 mM HEPES, pH7.4 containing 150 mM NaCl, 3 mM EDTA and 0.01% surfactant P20. Data were analyzed with BIAevaluation 4.1 software. The collected data were aligned and buffer blanks were subtracted from each sensorgrams prior to normalization. When the data fitted 1:1 binding model, $k_d$ was calculated as described (Zhang et al, 2004).

To rank the dissociations of binders in the unavailability of their $k_d$ data, dissociation diagrams of the binders are normalized to 100 at the start of their dissociations. This analysis allows easy visual identification of fast, medium and slow associations of the bindings, which represent low, medium and high affinities for the binders.

Figure 5:
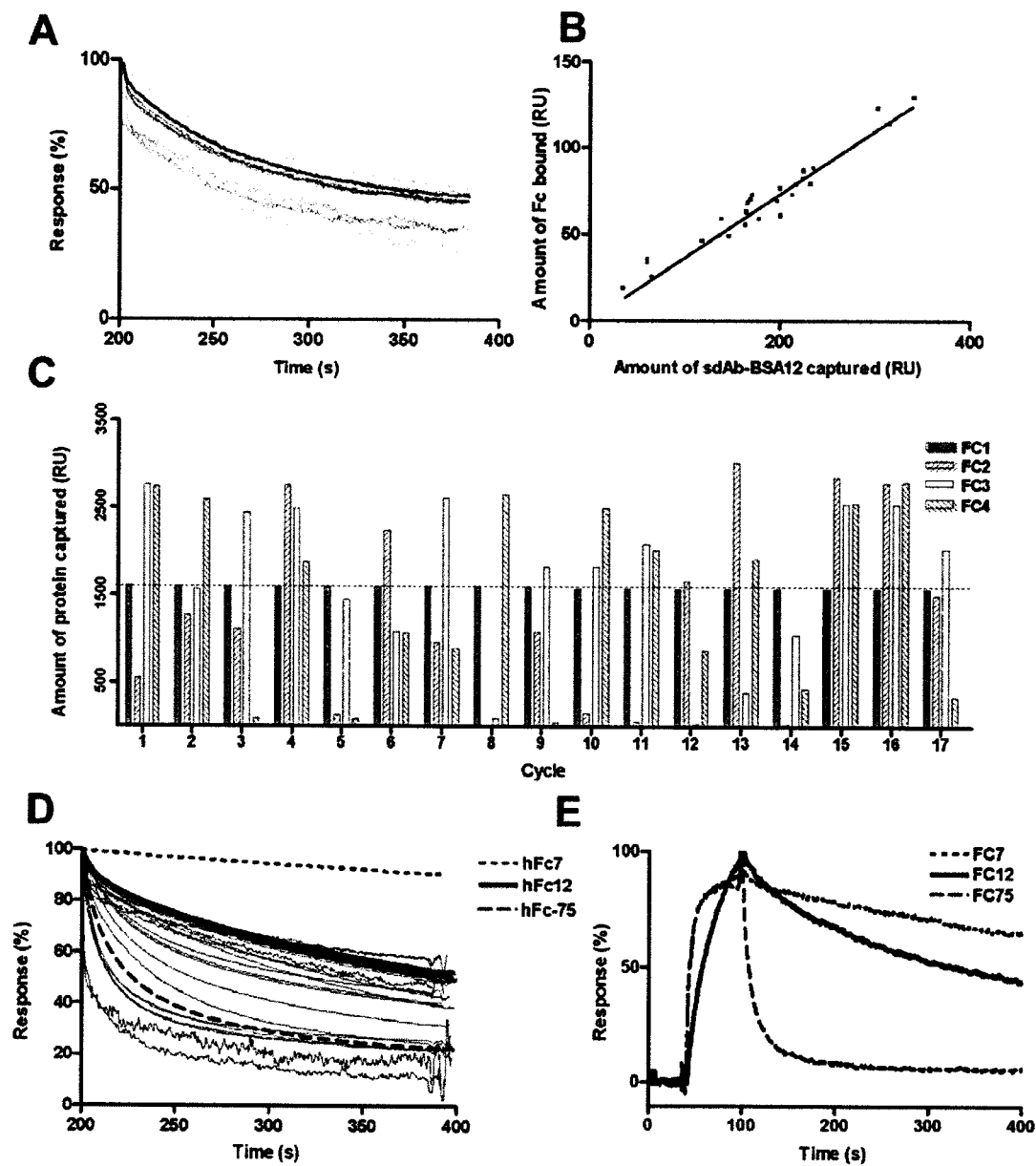
FIG. 5 shows results of $k_d$ ranking.

The accuracy and reproducibility of such measurements were first investigated using samples from 27 independent transformants of the same clone FC17-BSA12 (FIG. 5A). 23 of the 27 dissociation profiles are nearly identical (FIG. 5A, upper group). Dissociation profiles of four sdAb-BSA12s (FIG. 5A, lower group) have slightly different profiles. This is very likely because these four isolates have lower concentrations than the others, and errors caused by switching from antigen injection to dissociation made a bigger impact on the data. Although Fc is a dimeric antigen, the dissociation data during the first 30 s fitted 1:1 binding model nicely, and initial $k_d$s for the 27 Fc17-BSA12s were calculated as $8 \times 10^{-3}$ 1/s±SD 6.7%. The small SD value strongly suggests that this approach of affinity determination can provide reliable and reproducible data. Furthermore, the amounts of Fc bound to Fc17-BSA12 at the end of injection were linear-correlated to the amounts by Fc17-BSA12 captured on BSA (FIG. 5B).

Another set of 51 transformants representing 12 different sdAb clones were then subjected to analysis of their dissociation profiles using Biacore 3000 with a Sensorchip CM5 which can monitor four flow cells simultaneously. This was achieved through 17 rounds of capturing sdAb-BSA12 on pre-immobilized BSA surfaces, measuring bindings of human Fc to sdAb-BSA12 and subsequent regeneration of the BSA surfaces. In each round one flow cell was used to capture purified BSA12 to investigate the stability of the BSA surface, which is very important if automation of affinity ranking is required. The other three flow cells were used to capture sdAb-BSA12s and subsequent determination of their dissociation profiles.

The immobilized BSA was very resilient to the employed regeneration buffer. The amounts of BSA12 captured in all 17 rounds were practically identical (FIG. 5C). This provides a solid basis for ranking $k_d$s of a large number of clones in an automated manner.

More than 500 RUs of sdAb-BSA12s were captured for the majority of the constructs, yet only less than 40 RUs were observed for eight of the clones (FIG. 5C). Dissociation data of the eight binders were poor, probably because of the low surface capacity, and were not further analyzed.

All of the rest 43 sdAb-BSA12s showed specific bindings to Fc (FIG. 5D). 22 of them reached equilibrium or near equilibrium within the injection time of 3 min (data not shown). The data were normalized to facilitate comparison of their dissociation patterns. Although an accurate $k_d$ can not be obtained for most of the interactions, normalization of the dissociation profiles still provided an easy way to rank the rates of the dissociations. Different isolates from the same clone again had near identical profiles (data not shown), reaffirming the reproducibility of the data generated through this approach. The majority of the constructs had a dissociation profiles similar to that of Fc12-BSA12 (highlighted in thick solid line). One of the constructs, Fc7-BSA12 (thick dotted line), had an obviously slower dissociation than others. Some constructs, such as Fc75-BSA12 (thick dashed line), had relatively fast dissociations.

To assess whether ranking of the dissociations by injecting an antigen onto sdAb-BSA12 surfaces reflects ranking of their real affinities, three sdAbs Fc7, Fc12 and Fc75 were expressed and purified as monomeric sdAbs and their affinities measured by injecting them onto an Fc surface. The affinities of Fc7, Fc12 and Fc75 were calculated as $2 \times 10^{-9}$ M, $7 \times 10^{-8}$ M and $6 \times 10^{-7}$ M, respectively, and their fittings into the 1:1 biding model are good. The order of the affinities (FIG. 5E) was the same as that obtained from dissociation ranking using FASEBA (FIG. 5D), suggesting that injecting an antigen to its Binder-BSA12 surface after the latter being captured by BSA allows ranking of the affinities of the binders. Combination of FASEBA with SPR instrument allowing injection of multiple concentrations of ligands (available in the market) would generate accurate $K_D$ data, if the antigen is monomeric.

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

Sequences

SEQ ID NO: 1
CAGGTAAAGCTGGAGGAGTCTGGGGGAGGACTGGTGCAGGTTGGGGACT

CTCTGAGACTCTCCTGTGCAGCCTCCGGACGCACCTTCAGTAACTATAC

CATGGCCTGGTTCCGCCAGTTTCCAGGGAAGGAGCGTGAGTTTGTAGCA

GTAGTTAGTCGGGGGGTGGCGCCACAGACTATGCAGACTCCGTGAAGG

GCCGATTCACCATCTCCAGAGACAACGCCAAGAACACCATGTATCTGCA

AATGAACAGCCTGAAAACTGAGGACACGGCCGTCTATTACTGTGCAGCG

GGTACAGACCTAAGTTACTATTACAGCACAAAAAAATGGGCCTACTGGG

GCCAGGGGACCCAGGTCACCGTCTCCTCA

SEQ ID NO: 2
QVKLEESGGGLVQVGDSLRLSCAASGRTFSNYTMAWFRQFPGKEREFVA

VVSRGGGATDYADSVKGRFTISRDNAKNTMYLQMNSLKTEDTAVYYCAA

GTDLSYYYSTKKWAYWGQGTQVTVSS

SEQ ID NO: 3
TAGAGGGTAGAATTCATGAAAAAAACCGCTATCGCGATCGCAGTTGCAC

TGGCTGGTTTCGCTACCGTTGCGCAGGCCCAGCCGGCCCAGGTGCACCT

GCAGTCTGCGGCCGCGGGCCAGGCCGGCCAGGGATCCGGTGGAGGCGGG

TCCGGTGGAGGCGGGTCCGGTGGAGGCGGGTCCCAGGTAAAGCTGGAGG

AGTCTGGGGGAGGACTGGTGCAGGTTGGGGACTCTCTGAGACTCTCCTG

TGCAGCCTCCGGACGCACCTTCAGTAACTATACCATGGCCTGGTTCCGC

CAGTTTCCAGGGAAGGAGCGTGAGTTTGTAGCAGTAGTTAGTCGGGGG

GTGGCGCCACAGACTATGCAGACTCCGTGAAGGGCCGATTCACCATCTC

CAGAGACAACGCCAAGAACACCATGTATCTGCAAATGAACAGCCTGAAA

ACTGAGGACACGGCCGTCTATTACTGTGCAGCGGGTACAGACCTAAGTT

ACTATTACAGCACAAAAAAATGGGCCTACTGGGCCAGGGGACCCAGGT

CACCGTCTCCTCAGATCTGAACCATCACCATCACCATCACTAGTGAAAG

CTTGGCACTGGCCGTCGTTTTACAACGTCGTGACTGGGAAAACCCTGGC

GTTACCCAACTTAATCGCCTTGCAGCACATCCCCCTTTCGCCAGCTGGC

GTAATAGCGAAGAGGCCCGCACCGATCGCCCTTCCAACAGTTGCGCAGC

CTGAATGGCGAATGGCGCCTGATGCGGTATTTTCTCCTTACGCATCTGT

GCGGTATTTCACACCGCATATGGTGCACTCTCAGTACAATCTGCTCTGA

TGCCGCATAG

REFERENCES

All patents, patent applications and publications referred to herein and throughout the application are hereby incorporated by reference.

Arbabi-Ghahroudi, M., Tanha, J. & MacKenzie, R. (2009b). Isolation of monoclonal antibody fragments from phage display libraries. *Methods Mol Biol* 502, 341-64.

Arbabi-Ghahroudi, M., To, R., Gaudette, N., Hirama, T., Ding, W., MacKenzie, R. & Tanha, J. (2009a). Aggregation-resistant VHs selected by in vitro evolution tend to have disulfide-bonded loops and acidic isoelectric points. *Protein Eng Des Sel* 22, 59-66.

Arbabi-Ghahroudi, M., To, R., Gaudette, N., Hirama, T., Ding, W., Mackenzie, R. & Tanha, J. (2008). Aggregation-resistant VHs selected by in vitro evolution tend to have disulfide-bonded loops and acidic isoelectric points. *Protein Eng Des Sel*.

Binz, H. K., Amstutz, P., Kohl, A., Stumpp, M. T., Briand, C., Forrer, P., Grutter, M. G. & Pluckthun, A. (2004). High-affinity binders selected from designed ankyrin repeat protein libraries. *Nat Biotechnol* 22, 575-82.

Christ, D., Famm, K. & Winter, G. (2007). Repertoires of aggregation-resistant human antibody domains. Protein Eng Des Sel 20, 413-6.

Dumoulin, M., Conrath, K., Van Meirhaeghe, A., Meersman, F., Heremans, K., Frenken, L. G., Muyldermans, S., Wyns, L. & Matagne, A. (2002). Single-domain antibody fragments with high conformational stability. *Protein Sci* 11, 500-15.

Ewert, S., Honegger, A. & Pluckthun, A. (2003). Structure-based improvement of the biophysical properties of immunoglobulin VH domains with a generalizable approach. *Biochemistry* 42, 1517-28.

Famm, K., Hansen, L., Christ, D. & Winter, G. (2008). Thermodynamically stable aggregation-resistant antibody domains through directed evolution. *J Mol Biol* 376, 926-31.

Hamers-Casterman, C., Atarhouch, T., Muyldermans, S., Robinson, G., Hamers, C., Songa, E. B., Bendahman, N. & Hamers, R. (1993). Naturally occurring antibodies devoid of light chains. *Nature* 363, 446-8.

Honegger, A., Malebranche, A. D., Rothlisberger, D. & Pluckthun, A. (2009). The influence of the framework core residues on the biophysical properties of immunoglobulin heavy chain variable domains. *Protein Eng Des Sel* 22, 121-34.

Jespers, L., Schon, O., Famm, K. & Winter, G. (2004). Aggregation-resistant domain antibodies selected on phage by heat denaturation. *Nat Biotechnol* 22, 1161-5.

Jonsson, A., Dogan, J., Herne, N., Abrahmsen, L. & Nygren, P. A. (2008). Engineering of a femtomolar affinity binding protein to human serum albumin. *Protein Eng Des Sel* 21, 515-27.

Kery, V., Savage, J. R., Widjaja, K., Blake, B. K., Conklin, D. R., Ho, Y. S., Long, X., von Rechenberg, M., Zarembinski, T. I. & Boniface, J. J. (2003). Expression screen by enzyme-linked immunofiltration assay designed for high-throughput purification of affinity-tagged proteins. *Anal Biochem* 317, 255-8.

Kohl, A., Binz, H. K., Forrer, P., Stumpp, M. T., Pluckthun, A. & Grutter, M. G. (2003). Designed to be stable: crystal structure of a consensus ankyrin repeat protein. *Proc Natl Acad Sci USA* 100, 1700-5.

Lehmann, M., Kostrewa, D., Wyss, M., Brugger, R., D'Arcy, A., Pasamontes, L. & van Loon, A. P. (2000). From DNA sequence to improved functionality: using protein sequence comparisons to rapidly design a thermostable consensus phytase. *Protein Eng* 13, 49-57.

Leonard, P., Safsten, P., Hearty, S., McDonnell, B., Finlay, W. & O'Kennedy, R. (2007). High throughput ranking of recombinant avian scFv antibody fragments from crude lysates using the Biacore A100. *J Immunol Methods* 323, 172-9.

Li, S., Zheng, W., Kuolee, R., Hirama, T., Henry, M., Makvandi-Nejad, S., Fjallman, T., Chen, W. & Zhang, J. (2009). Pentabody-mediated antigen delivery induces antigen-specific mucosal immune response. *Mol Immunol* 46, 1718-1726.

Niesen, F. H., Koch, A., Lenski, U., Harttig, U., Roske, Y., Heinemann, U. & Hofmann, K. P. (2008). An approach to quality management in structural biology: biophysical selection of proteins for successful crystallization. *J Struct Biol* 162, 451-9.

Saerens, D., Pellis, M., Loris, R., Pardon, E., Dumoulin, M., Matagne, A., Wyns, L., Muyldermans, S. & Conrath, K. (2005). Identification of a universal VHH framework to graft non-canonical antigen-binding loops of camel single-domain antibodies. *J Mol Biol* 352, 597-607.

Schmid, F. X. (1997). Optical Spetroscopy to Characterize Protein Conformation and Conformational Change. In *Protein Structure, A Practical Approach* (Creighton, T. E., ed.), pp. 266-297. Oxford University Press.

Tanha, J., Muruganandam, A. & Stanimirovic, D. (2003). Phage display technology for identifying specific antigens on brain endothelial cells. *Methods Mol Med* 89, 435-49.

To, R., Hirama, T., Arbabi-Ghahroudi, M., MacKenzie, R., Wang, P., Xu, P., Ni, F. & Tanha, J. (2005). Isolation of monomeric human V(H)s by a phage selection. *J Biol Chem* 280, 41395-403.

Ueda, H., Kristensen, P. & Winter, G. (2004). Stabilization of antibody V-H-domains by proteolytic selection. *Journal of Molecular Catalysis B Enzymatic* 28, 173-179.

Woestenenk, E. A., Hammarstrom, M., Hard, T. & Berglund, H. (2003). Screening methods to determine biophysical properties of proteins in structural genomics. *Anal Biochem* 318, 71-9.

Zhang, J., Tanha, J., Hirama, T., Khieu, N. H., To, R., Tong-Sevinc, H., Stone, E., Brisson, J. R. & MacKenzie, C. R. (2004). Pentamerization of single-domain antibodies from phage libraries: a novel strategy for the rapid generation of high-avidity antibody reagents. *J Mol Biol* 335, 49-56.

PCT/US2009/60495, entitled Induction of Mucosal Immune Responses by Mucosal Delivery Pentabody Complex (MDPC), filed on Oct. 13, 2009.

WO 2010/043057.

---

The invention claimed is:

1. A method for screening of protein candidates, comprising:
   a) providing fusion proteins, each fusion protein comprising one protein candidate and a protein anchor, wherein the protein anchor is an antibody or antibody fragment comprising a complementarity determining region (CDR)1 sequence of NYTMA (SEQ ID NO:11); a CDR2 sequence of VVSRGGGATDYADSVKG (SEQ ID NO:12); and a CDR3 sequence of GTDLSYYYSTKKWAY (SEQ ID NO:13); and
   b) evaluating the expression levels of the protein candidates; or
   c) evaluating the biophysical properties of the protein candidates; or
   d) evaluating the binding kinetics of the protein candidate; or
   e) any combination of steps b) to d) above,
wherein the protein anchor binds to a specific coating thus capturing the protein candidates and facilitating the evaluation of expression levels, biophysical characteristics and binding kinetics; and wherein the specific coating is bovine serum albumin.

2. The method of claim 1, wherein:
the step of evaluating the expression levels of the protein candidates (step b) is achieved by
   i. binding the protein anchor to a specific coating on a solid surface; and
   ii. measuring the amount of bound fusion proteins; or the step of evaluating the biophysical properties of the protein candidates (step c) is achieved by
   i. denaturing the fusion proteins;
   ii. allowing the denatured fusion proteins to refold;
   iii. filtering sample containing the refolded fusion proteins;
   iv. binding the protein anchor to a specific coating on a solid surface;
   v. measuring the amount of bound fusion proteins; and
   vi. comparing the amount of bound fusion proteins to that obtained in step b); or the step of evaluating the binding kinetics of the protein candidate (step d) is achieved by
   i. binding the protein anchor to a specific coating on a solid surface; and
   ii. measuring the binding kinetics of the protein candidates to their target/antigen by allowing the target/antigen to bind to the protein candidates and observing their associations and dissociations.

3. The method of claim 1, wherein the protein anchor
   a) has high affinity to its specific coating;
   b) has an interaction with its specific coating that can be easily disrupted;
   c) exists in monomeric form and has high thermostability;
   d) is highly specific to its specific coating; or
   e) any combination of a) to d).

4. The method of claim 1, wherein the antibody or fragment thereof comprises the sequence of BSA12 (SEQ ID NO. 2) or a mutant or fragment thereof.

5. The method of claim 1, wherein expression levels are measured by ELISA.

6. The method of claim 2, wherein the denaturation is by exposure to heat or extreme pH.

7. The method of claim 1, wherein the binding kinetics are measured by surface plasmon resonance.

* * * * *